(12) United States Patent
Ensign et al.

(10) Patent No.: US 6,379,388 B1
(45) Date of Patent: Apr. 30, 2002

(54) TIBIAL PROSTHESIS LOCKING SYSTEM AND METHOD OF REPAIRING KNEE JOINT

(75) Inventors: Michael D. Ensign; Scott Shaver, both of Draper; Michael H. Bourne; E. Marc Mariani, both of Salt Lake City, all of UT (US)

(73) Assignee: Ortho Development Corporation, Draper, UT (US)

( * ) Notice: Subject to any disclaimer, the term of this patent is extended or adjusted under 35 U.S.C. 154(b) by 0 days.

(21) Appl. No.: 09/458,111

(22) Filed: Dec. 8, 1999

(51) Int. Cl.[7] ................................................. A61F 2/38
(52) U.S. Cl. ................................ 623/20.34; 623/20.32; 623/20.21; 623/20.28
(58) Field of Search ........................... 623/16.11, 18.11, 623/20.14, 20.15, 20.21, 20.28, 20.32, 20.34, FOR 116

(56) References Cited

U.S. PATENT DOCUMENTS

| | | |
|---|---|---|
| 4,209,861 A | 7/1980 | Walker et al. |
| 4,213,209 A | 7/1980 | Insall et al. |
| 4,224,697 A | 9/1980 | Murray et al. |
| 4,249,270 A | 2/1981 | Bahler et al. |
| 4,298,992 A | 11/1981 | Burstein et al. |
| 4,353,136 A | 10/1982 | Polyzoides et al. |
| 4,634,444 A | 1/1987 | Noiles |
| 4,714,474 A | 12/1987 | Brooks, Jr. et al. |
| 4,822,362 A | 4/1989 | Walker et al. |
| 4,888,021 A | 12/1989 | Forte et al. |
| 4,892,547 A | 1/1990 | Brown |
| 4,950,297 A | 8/1990 | Elloy et al. |
| 4,950,298 A | 8/1990 | Gustilo et al. |
| 4,959,071 A | 9/1990 | Brown et al. |
| 5,007,933 A | 4/1991 | Sidebotham et al. |
| 5,011,496 A | 4/1991 | Forte et al. |
| 5,116,376 A | 5/1992 | May |
| 5,147,405 A | 9/1992 | Van Zile et al. |
| 5,152,796 A | 10/1992 | Slamin |
| 5,181,925 A | 1/1993 | Houston et al. |
| 5,194,066 A | 3/1993 | Van Zile |

(List continued on next page.)

FOREIGN PATENT DOCUMENTS

| | | | |
|---|---|---|---|
| EP | 0 103 697 A1 | 7/1983 | |
| EP | 0 294 298 A1 | 5/1988 | |
| EP | 495340 A1 * | 7/1992 | ................ 623/20 |
| FR | 2701387 A1 | 2/1993 | |

OTHER PUBLICATIONS

Johnson & Johnson, The P.F.C. Modular Total Knee System; Jan. 1991, Brit JBJS.
Orthomet, Inc., The Orthomet AXIOM Total Knee, Jan. 1993, JBJS.
Smith & Nephew Richards; The Genesis Total Knee System; no date available.
English translation of European Patent No. 0 495 350 A1, dated Jul. 22, 1992.

*Primary Examiner*—Jeffrey A. Smith
(74) *Attorney, Agent, or Firm*—Clayton, Howarth & Cannon, P.C.

(57) ABSTRACT

A tibial prosthesis locking system. The system includes a tibial plate and an articular surface component or tibial insert. A proximal side of the tibial plate includes perimeter sidewalls with holding flanges formed thereon, and male retaining projections are formed on interior portions of the proximal tibial plate. A distal side of the articular surface component is designed to interlock with the holding flanges and retaining projections formed on the tibial plate. The male retaining projections and the holding flanges cooperatively engage with the articular surface component to provide it with resistance to movement in an anterior-posterior direction, a medial lateral direction, a rotational direction, and a vertical direction.

50 Claims, 4 Drawing Sheets

U.S. PATENT DOCUMENTS

| | | |
|---|---|---|
| 5,201,881 A | 4/1993 | Evans |
| 5,236,461 A | 8/1993 | Forte |
| 5,271,737 A * | 12/1993 | Baldwin et al. ......... 623/20.34 |
| 5,330,534 A | 7/1994 | Herrington et al. |
| 5,358,530 A | 10/1994 | Hodorek |
| 5,370,699 A | 12/1994 | Hood et al. |
| 5,405,396 A | 4/1995 | Heldreth et al. |
| 5,549,686 A | 8/1996 | Johnson et al. |
| 5,609,643 A | 3/1997 | Colleran et al. |
| 5,609,644 A | 3/1997 | Ashby et al. |
| 5,645,604 A | 7/1997 | Schneider et al. |
| 5,702,461 A | 12/1997 | Pappas et al. |
| 5,702,463 A | 12/1997 | Pothier et al. |
| 5,702,464 A | 12/1997 | Lackey et al. |
| 5,702,469 A | 12/1997 | Whipple et al. |
| 5,776,202 A | 7/1998 | Copf et al. |
| 5,782,925 A * | 7/1998 | Collazo et al. |
| 5,824,104 A | 10/1998 | Tuke |
| 5,871,545 A * | 2/1999 | Goodfellow et al. ..... 623/20.28 |
| 6,090,144 A * | 7/2000 | Letot et al. .............. 623/20.34 |

\* cited by examiner

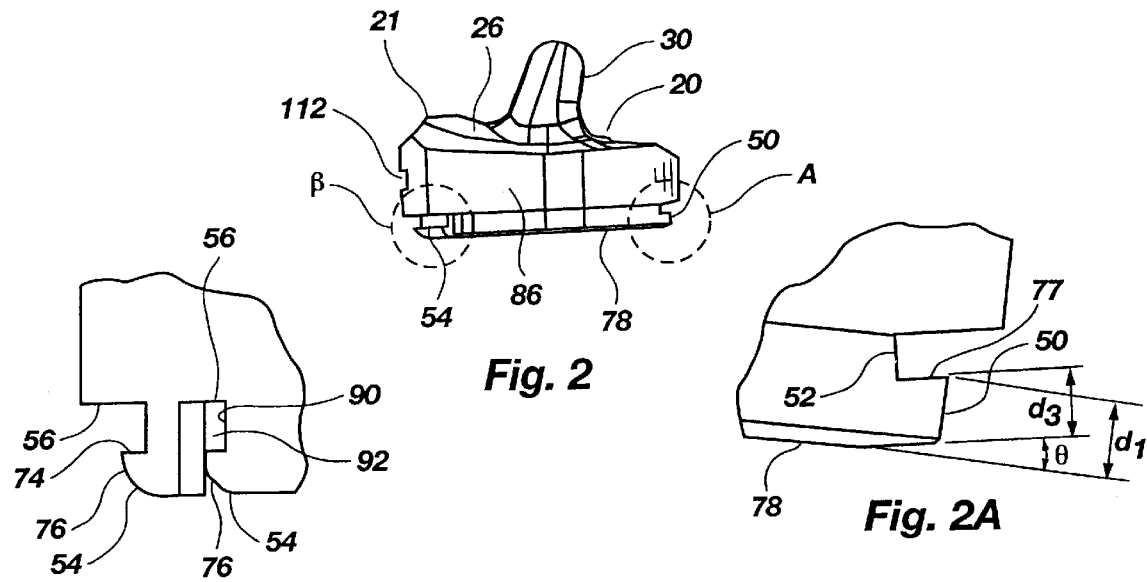
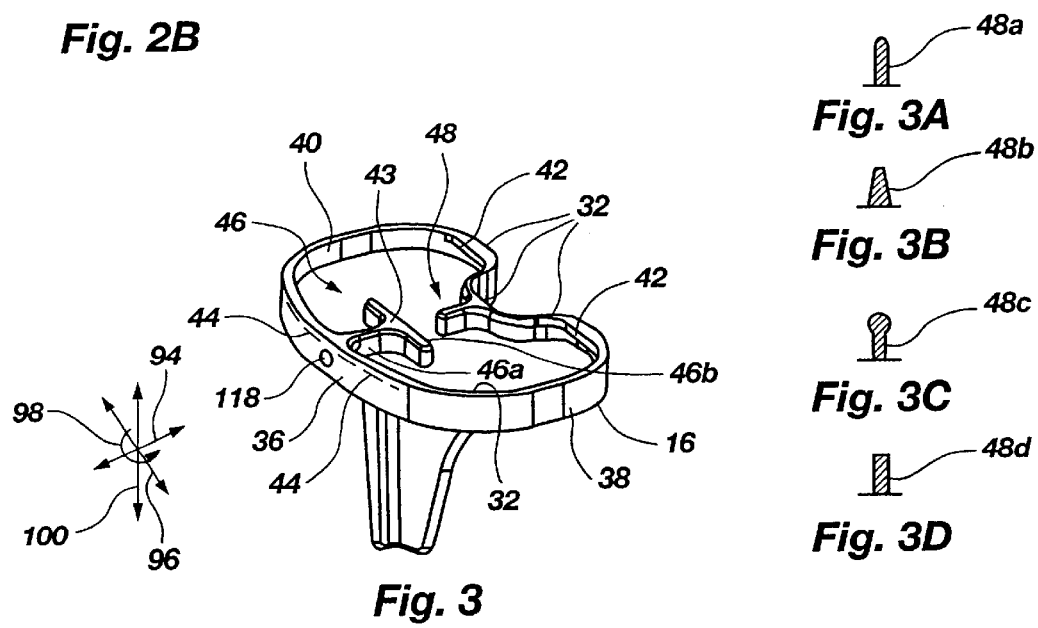
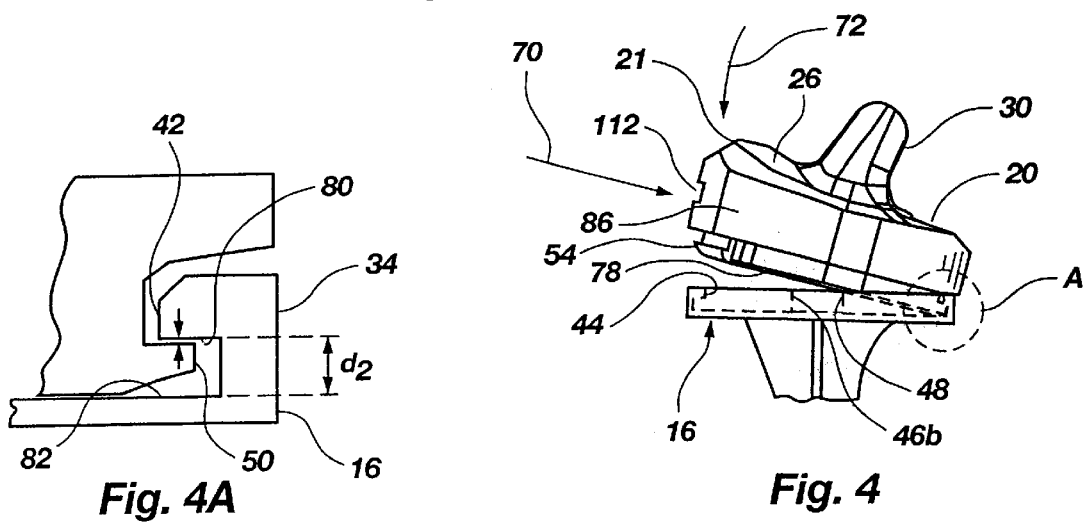

TIBIAL PROSTHESIS LOCKING SYSTEM AND METHOD OF REPAIRING KNEE JOINT

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. The Field of the Invention

The present invention relates generally to the replacement of the proximal tibial surface of a knee joint, and more particularly, but not entirely, to a locking system for attaching together the components of a tibial prosthesis.

2. Description of Related Art

It is known to construct a modular tibial prosthesis having a base plate and a separate articular surface component. It is advantageous to utilize a separate component for the articular surface so that it can be made from different material than the base plate. More specifically, since the base plate is implanted directly into cancellous bone in the proximal end of the tibia, it is typically made from titanium steel for reasons known to those skilled in the field, including the fact that titanium is strong, relatively lightweight, and biocompatible. Since titanium does not operate well as a bearing surface, a separate piece, typically made from a polymer, is attached to the base plate to operate as an articulating surface in sliding, frictional engagement with the distal femur, which typically comprises a femoral component having a pair of articulating condyles.

Modular tibial prostheses utilizing a base plate and a separately attachable articular surface component require a reliable means for attaching the articular surface component to the base plate. It is important to achieve secure fixation between those components without unduly weakening one or both of them. These objectives are difficult to obtain because of the significant loads imposed on the articular surface component by the distal femur, especially in the case of a "posterior stabilized" knee. The phrase "posterior stabilized" knee refers to a prosthetic knee joint having a spine element extending upwardly from the tibial plate that is constrained and guided in its motion by femoral condyles and by a cam component that limits the point of maximum flexion of the knee, to compensate for removal of the posterior cruciate ligament ("PCL"). Conversely, the phrase "cruciate retaining" knee refers to a prosthetic knee joint without the cam and spine element because the knee motion is sufficiently constrained and guided by the presence of a working PCL.

Attempts have been made in the prior art to provide a modular tibial prosthesis that has an effective mechanism for attaching the articular surface component to the base plate. U.S. Pat. Nos. 5,405,396 (Heldreth et al.), U.S. Pat. No. 4,822,362 (Walker et al.); U.S. Pat. No. 5,194,066 (Van Zile) and U.S. Pat. No. 5,609,644 (Ashby et al.) each disclose attachment systems for attaching a separate articular surface component to a tibial base plate. The Heldreth et al. patent (U.S. Pat. No. 5,405,396) utilizes a dovetail structure at item 7, shown in FIG. 2, for retaining the articular surface. The Walker et al. patent (U.S. Pat. No. 4,822,362) teaches tongue-in-groove interlock ledges 28, as shown in FIGS. 1 and 5–6, to retain the articular surface component. The Van Zile patent (U.S. Pat. No. 5,194,066) uses parallel male projections shown in FIGS. 2–3 for the retaining action. The Ashby et al. patent (U.S. Pat. No. 5,609,644) uses a peg-in-slot engagement, shown in FIG. 8 (peg 7 engages within slot 17, and pin 20 engages within slot 19). None of these patents, or any of the others known to applicants, addresses the challenge of providing highly effectively resistance to movement of the articular surface component in all directions while maintaining the thickness of the articular surface component at a minimum.

The prior art is thus characterized by several disadvantages that are addressed by the present invention. The present invention minimizes, and in some aspects eliminates, the above-mentioned failures, and other problems, by utilizing the methods and structural features described herein.

BRIEF SUMMARY AND OBJECTS OF THE INVENTION

It is therefore an object of the present invention to provide a tibial prosthesis locking system.

It is an additional object of the present invention to provide such a tibial prosthesis locking system that is simple in design and manufacture, and easier to use.

It is another object of the present invention, in accordance with one aspect thereof, to provide such a tibial prosthesis locking system that provides enhanced resistance to movement of an articular surface component of the prosthesis in at least four directions.

It is a further object of the present invention, in accordance with one aspect thereof, to provide such a tibial prosthesis locking system in which a thickness of an articular surface component of the prosthesis is maintained at a minimum.

The above objects and others not specifically recited are realized in a specific illustrative embodiment of a tibial prosthesis locking system. The system includes a tibial plate and an articular surface component or tibial insert. A proximal side of the tibial plate includes perimeter sidewalls with holding flanges formed thereon, and male retaining projections are formed on interior portions of the proximal tibial plate. A distal side of the articular surface component is designed to interlock with the holding flanges and retaining projections formed on the tibial plate. The male retaining projections and the holding flanges cooperatively engage with the articular surface component to provide it with resistance to movement in an anterior-posterior direction, a medial lateral direction, a rotational direction, and a vertical direction.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 2 is a side view of an articular surface component of the tibial prosthesis of FIG. 1;

FIG. 2A is a side, break-away view of a posterior portion of the articular surface component of FIG. 2, taken along section A of FIG. 2;

FIG. 2B is a side, break-away view of an anterior portion of the articular surface component of FIG. 2, taken along section B of FIG. 2;

FIG. 3 is a perspective view of a tibial plate of the tibial prosthesis of FIG. 1;

FIG. 3A is a cross-sectional view of a male projection formed in the tibial plate of FIG. 3;

FIG. 3B is a cross-sectional view of an alternative embodiment of the male projection of FIG. 3A;

FIG. 3C is a cross-sectional view of another alternative embodiment of the male projection of FIG. 3A;

FIG. 3D is a cross-sectional view of still another alternative embodiment of the male projection of FIG. 3A;

FIG. 4 is a side, schematic view of the tibial prosthesis of FIG. 1, illustrating the locking system and method;

FIG. 4A is a side, break-away view of a posterior portion of the tibial prosthesis of FIG. 4, taken along section A of FIG. 4;

DETAILED DESCRIPTION OF THE INVENTION

Figure 1:
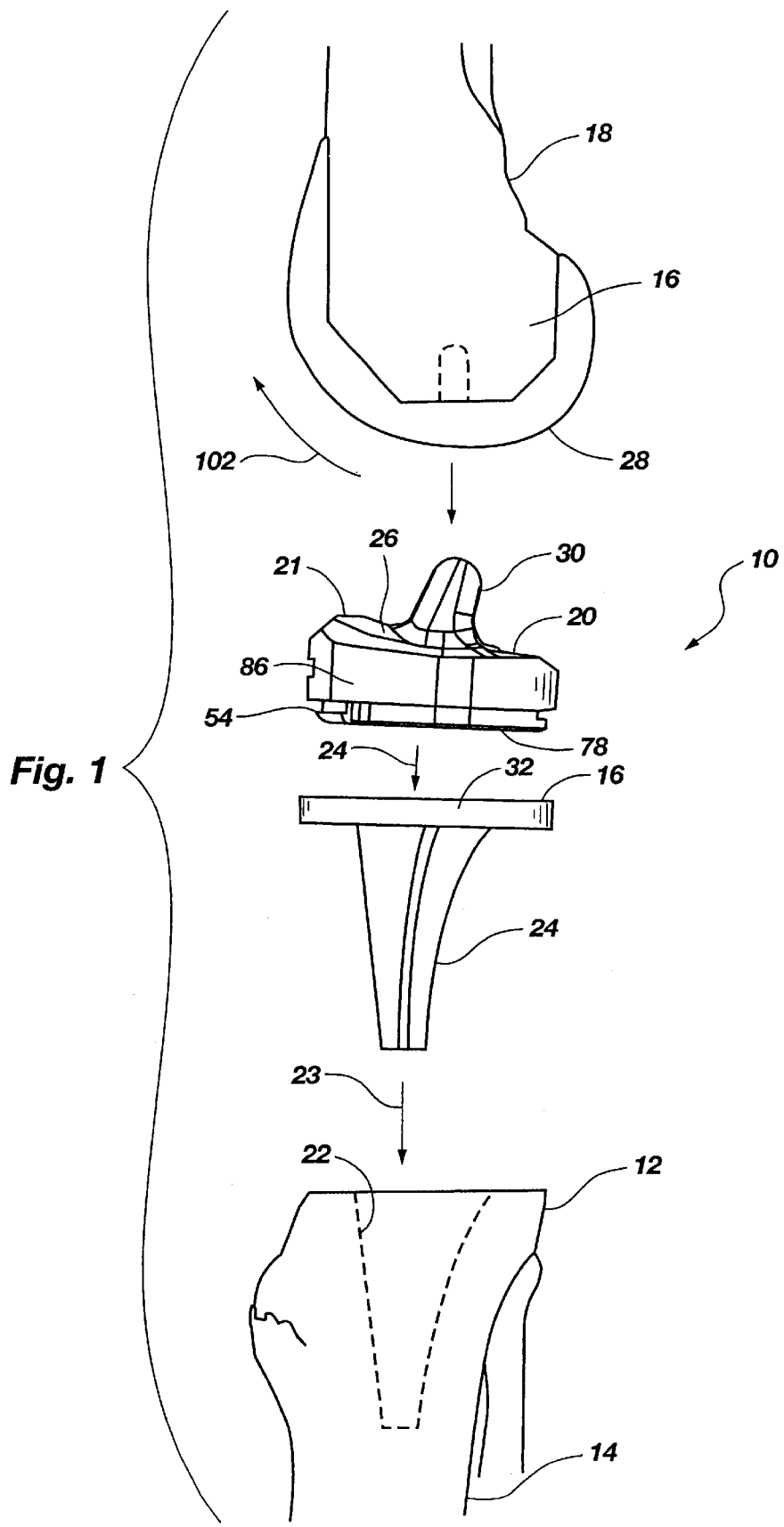
FIG. 1 is an exploded, schematic view of a tibial prosthesis and locking system made in accordance with the principles of the present invention, in association with a proximal portion of a tibia and a distal portion of a femur.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Applicants have developed a unique modular tibial prosthesis design that provides enhanced resistance to movement of an articular surface component of the prosthesis in at least four directions. The design includes several key components that provide unique locking attachment between a tibial plate and a separate articular surface component, without requiring increased thickness of the articular surface component.

Referring now to FIG. 1, there is shown an exploded view of a tibial prosthesis, designated generally at 10, made in accordance with the present invention and in association with a proximal portion 12 of a tibia 14 and a distal portion 17 of a femur 18. The tibial prosthesis 10 includes a tibial plate 16 and an articular surface component, or tibial insert, 20.

In operation, a resection surface 22 is prepared in cancellous bone in the proximal portion of the tibia 14 for receiving a keel 24 of the tibial plate 16 thereinto, indicated by arrow 23. The tibial insert 20 is snapped into engagement upon the tibial plate 16 in part by downward vertical movement indicated by arrow 25. The tibial insert 20 includes articular, bearing surfaces 26 formed on the proximal side thereof for sliding, frictional engagement with the distal portion 17 of the femur 18. The femur 18 may have femoral condyles 28 attached thereto as understood to those of ordinary skill in the field of knee prostheses. The femoral condyles 28 reside in sliding, frictional contact upon the articular bearing surfaces 26 of the tibial insert 20 and thereby operate as a knee joint replacement. The femoral condyles 28 include a cam member (not shown) for engaging against a spine 30 of the tibial insert 20 at a maximum desired flexion position, for reducing mechanical stress in the components and inhibiting subluxation.

Reference will now be made to FIGS. 1–8 collectively, with specific reference made to particular drawings when specified below, but with the understanding that reference numerals and component parts shall be referred to in connection with all of the drawings.

The tibial plate 16 includes a perimeter sidewall 32, which is preferably continuous and preferably extends around the entire perimeter. The sidewall 32 includes a posterior sidewall portion 34, an anterior sidewall portion 36, and, assuming the prosthesis 10 is implanted in the right knee of a patient, a medial sidewall portion 38 and a lateral sidewall portion 40. Posterior holding flanges 42 extend outwardly from the posterior sidewall 34, and anterior holding flanges 44 (shown in phantom line in FIGS. 3 and 4) extend outwardly from the anterior sidewall 36.

Formed on interior portions of the tibial plate 16 are male projections, or rails, 46 and 48. The rail 46 preferably comprises a "T" shape as shown, and may be described herein as a first rail 46a and second rail 46b, or alternatively a rail 46 having a first portion 46a and a second portion 46b.

The tibial insert 20 includes depressable flanges 50 extending outwardly from a posterior edge 52 of the tibial insert 20. The depressable flanges 50 may also be referred to posterior flanges. The tibial insert 20 further includes resilient locking members 54 extending in a downward direction from an anterior edge 56 of the tibial insert 20. A distal side 55 of the tibial insert 20 includes recesses 56 and 58 formed therein. The recesses 56 and 58 are configured, dimensioned and positioned for simultaneously receiving the rails 46 and 48 thereinto, respectively, such that the rails 46 and 48 are thereby positioned to engage against sidewalls defining the recesses 46 and 48 to thereby resist movement of the tibial insert 20.

The locking mechanism of the invention is accomplished collectively by a compressive interference fit between the posterior holding flanges 42 and the depressable flanges 50, respectively, and by a locking fit between the resilient locking members 54 and the anterior holding flanges 44, respectively, and preferably by a clamping fit between the recess 56 and rail 46 and the recess 58 and the rail 48, respectively. The clamping fit is preferably accomplished by making the rails 46 and 48 wider than the recess 56 and 58, respectively, such that the rails are forcibly inserted into the smaller recesses to thereby cause the recesses to clamp the rails.

The attachment of the tibial insert 20 onto the tibial plate 16 is accomplished as shown in FIG. 4. The tibial insert 20 is guided by a surgeon in a downward and posterior direction, as indicated by arrow 70, to thereby place the depressable flanges 50 into position beneath the posterior holding flanges 42. Thereafter, the tibial insert 20 is forced downwardly as indicated by arrow 72. The resilient locking members 54 each include a distal locking flange 74 formed thereon having a beveled edge 76, all being configured and dimensioned such that the downward vertical movement indicated by arrow 72 causes sliding frictional engagement of the beveled edges 76 against the anterior holding flanges 44 with a resulting inward depression of the resilient locking members 54 in a posterior direction, followed by a snap-lock movement of the distal locking flanges 74 in an anterior direction into place beneath the anterior holding flanges 44. It will be appreciated that the resilient locking members 54 are spaced apart from an anterior surface 90 of the tibial insert 20 by a space 92 (shown most clearly in FIG. 2B), to thereby enable inward depression of the locking members 54 in the posterior direction.

It will be appreciated that the compressive interference fit, indicated by the arrows in FIG. 4A, is accomplished cooperatively by the depressable flange 50 being angled upwardly by an angle 6 (shown most clearly in FIG. 2A) from a distal surface 78 of the tibial insert 20, and by the fact the distance $d_1$ is greater than distance $d_2$. The distance $d_1$, shown most clearly in FIG. 2A, is defined as the distance between an upper surface 77 of the depressable flange 50 and a lower surface 78 of the tibial insert 20 when the depressable flange 50 is in a natural, unbiased position. The distance $d_2$, shown most clearly in FIG. 4A, is defined as the distance between a lower surface 80 of the posterior holding flange 42 and an upper surface 82 of the tibial plate 16. The thickness $d_3$ of the depressable flange 50 (shown in FIG. 2A) being less than the space $d_2$ (shown in FIG. 4A) enables the depressable flange 50 to be non-forcibly inserted into position between the surfaces 80 and 82. The angle $\theta$ is preferably approximately eight degrees, but may comprise any suitable angle to accomplish the compressive interference fit described above. The tibial insert 20, being preferably constructed from a polymeric plastic material, possesses elastic memory which causes the flange 50 when depressed by the holding flange 42 to reside in compression.

Figure 7:
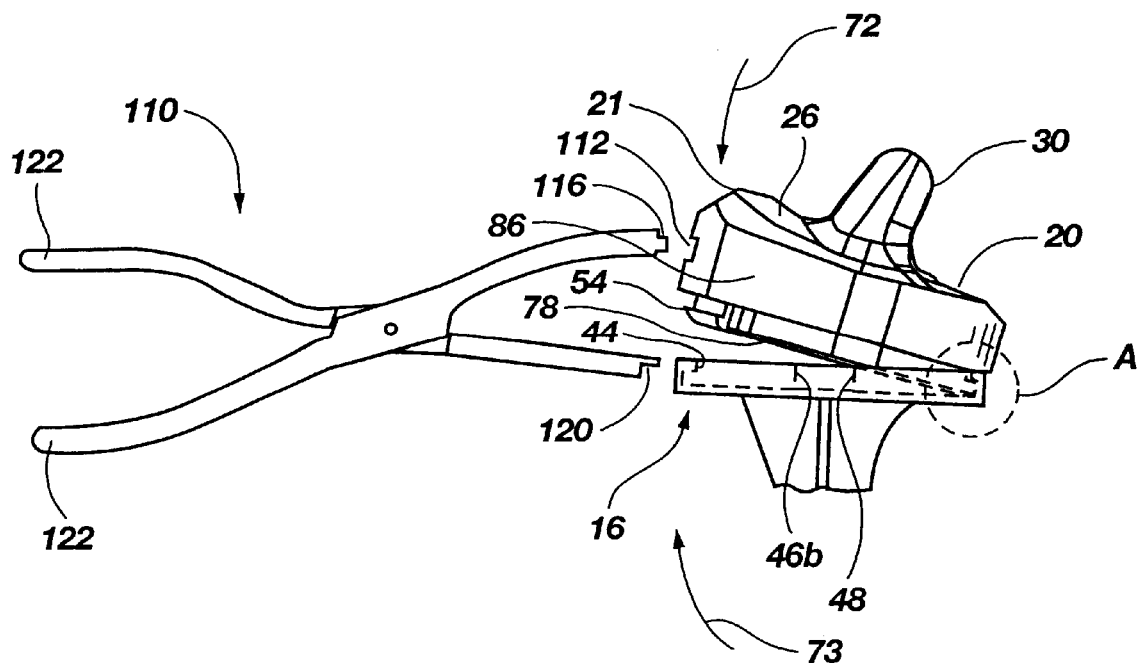
FIG. 7 is a side, schematic view of the tibial prosthesis of FIG. 4, in association with a grasping device.

Referring now to FIG. 7, it is shown that a grasping device 110 can be utilized to accomplish the downward force indicated by arrow 72. The tibial insert 20 includes a recess 112 that preferably includes an arcuate rear wall 114 as shown most clearly in FIG. 5. The device 110 has a mating insert 116 for insertion into the recess 112, the insert 116 preferably having an arcuate distal face that corresponds to the shape of the rear wall 114. A preferably round recess 118, shown most clearly in FIG. 3, is formed in the anterior sidewall 36 of the tibial plate 16, to correspond with an insert 120 of the device 110. A surgeon would insert the inserts 116 and 120 into the recesses 112 and 118, respectively, then grip the handles 122 of the device to thereby impose both the downward force 72 on the tibial insert 20 and also an upward force 73 on the tibial plate 16 to lock the locking members 54 in place beneath the anterior holding flanges 44 as explained above.

Referring now to FIGS. 3A, 3B, 3C and 3D, it will be appreciated that the rails 46 and 48 may embody any suitable cross sectional shape. Various embodiments are indicated in FIGS. 3A, 3B, 3C and 3D as 48a, 48b, 48c and 48d, respectively, and it is to be understood that said embodiments could be utilized for any rail formed on the tibial plate 16, including rail 46 or rail 48 or any other rail that might be formed in the tibial plate 16. A straight, parallel sided cross sectional shape 48a with a rounded upper side is shown in FIG. 3A. A tapered cross sectional shape 48b is shown in FIG. 3B. A straight, parallel sided cross sectional shape 48c, with an enlarged, bulbous upper end, is shown in FIG. 3C. A straight, parallel-sided cross sectional shape 48d, with a planer upper surface, is shown in FIG. 3D. Any other suitable shape may be utilized instead, as desired, and the inclusion of these four cross sectional shapes illustrate that a broad range of equivalents is supported herewith for any suitable shape to be used, whether presently known or later discovered.

For reference purposes, if the prosthesis 10 is implanted into a tibia of the right leg, the orientation will be to identify edge 86 of the tibial insert 20 as a medial side edge, and edge 88 as a lateral side edge. One advantageous aspect of the present invention is that the tibial insert 20 is preferably constructed such that, when the tibial insert 20 is initially locked into engagement on the tibial plate 16, a small space resides between the medial sidewall portion 38 on the tibial plate 16 and the medial side edge 86 of the tibial insert 20, and also between the lateral sidewall portion 40 on the tibial plate 16 and the lateral side edge 88 of the tibial insert 20. In the alternative, the prosthesis 10 may be constructed such that there is no such space between the medial and lateral portions of the tibial insert 20 and tibial plate 16, respectively, but in such cases it is preferred that any contact be slight and that there exist little or no compressive interference between those portions.

The advantages of configuring the prosthesis 10 such that either a small space or a non-interference contact exists between the medial and lateral portions of the tibial plate 16 and tibial insert 20, respectively, are that the tibial insert 20 is thereby enabled to settle into a position of stability on the tibial plate 16 without interference forces being imposed upon it from the medial or lateral sidewall portions 38 and 40 which might collectively impose an unwanted upward force on the tibial insert 20. It is to be understood that such small spacing or non-interfering contact may only be temporary as the tibial insert 20, being made of a polymer, will undergo some degree of creep and "cold flow" through use as an articular bearing surface against the femoral condyles 28 on the femur 18, and that the cold flow will be curbed by the perimeter sidewall 32, including the medial and lateral sidewall portions 38 and 40.

Referring now to FIG. 3 for orientation purposes, it will be appreciated that the interlocking elements described herein operate to provide highly effective resistance to movement of the tibial insert 20 in an anterior-posterior direction 94, a medial-lateral direction 96, a rotational direction 98, and a vertical direction 100, the rotational direction 98 being in reference to rotation about a vertical axis.

The rail 46 is particularly advantageous for providing resistance to movement of the tibial insert 20 in the anterior-posterior direction 94. By providing the portion 46a of the rail 46, which portion 46a preferably extends linearly in the medial-lateral direction 96 and at an interior area on the tibial plate 16 as shown, significantly increased surface area for resisting movement in the anterior-posterior direction is provided thereby. It will be appreciated that as the femoral condyles 28 engage in sliding frictional movement on the articular bearing surfaces 26 in direction 102 shown in FIG. 1, such movement will tend to impose a horizontal-anterior directed component of force upon the tibial insert 20, as those of ordinary skill in the field of physics will understand. Much of the impact of that horizontal-anterior directed component of force is resisted by the portion 46b of the rail 46 which, because of its orientation and its somewhat interior location on the tibial plate 16, provides much more effective resistance to movement in the anterior-posterior direction than simple reliance on the anterior sidewall 36 would provide.

The locking engagement between the resilient locking member 54 and the anterior holding flange 44 provides highly effective resistance to upward vertical movement of the tibial insert 20, in cooperation with the compressive interference fit between the posterior holding flanges 42 and the depressable flanges 50. Resistance to movement of the tibial insert 20 in the rotational direction 98 is enhanced by utilizing the combination of rails 46 and 48, and in particular by the fact that rail portion 46b extends in a transverse and preferably orthogonal direction relative to the rail portion 46a and the rail 48. Resistance to movement of the tibial insert 20 in the medial-lateral direction 96 is enhanced by the rail portion 46a and by the rail 48, which both face the medial-lateral direction.

Figures 5, 6:
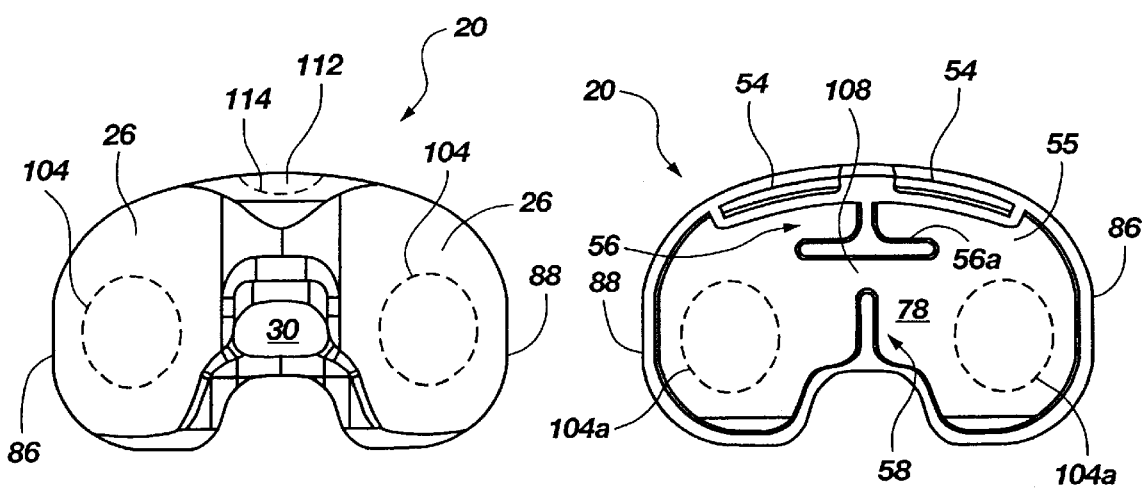
FIG. 5 is a plan view of the articular surface component of FIG. 1.
FIG. 6 is a view of the under side (distal side) of the articular surface component of FIG. 5.

It will be further understood that the articular bearing surfaces 26 are larger than the actual surface areas of contact that exist between the femoral condyles 28 and the tibial insert 20. The surface areas of contact vary in location and size on the bearing surfaces 26 depending on the position of the condyles 28, and are indicated schematically by the dashed boundary lines 104 in FIG. 5. Corresponding lines 104a are shown in FIG. 6, which is a view of the distal surface 78 of the tibial insert 20 of FIG. 5, to indicate boundaries of the surface areas of contact. The actual shape of the surface areas of contact is not necessarily circular as shown in FIGS. 5–6, but may be ovular or whatever contact area shape is caused. One of the important aspects of the invention is to address the competing objectives that the tibial insert 20 must be thick enough to operate as an articular bearing surface and withstand the significant loads imposed by the femoral condyles 28, but also must be as thin as possible to reduce the amount of necessary resection of the tibia 14. It is preferable that the tibial insert 20 be at least six millimeters (mm) thick at the surface areas of load contact 104. The invention strikes an optimal balance by providing the force resistance components mentioned above without causing a corresponding increase in the thickness of the tibial insert 20. This is accomplished in part by locating the rails 46 and 48 to reside between the surface area of contact boundaries 104 and thus out of vertical alignment with the direction of the vertical forces imposed on the tibial insert 20 by the femoral condyles 28. In other words, the rails 46 and 48 are preferably positioned such that they do not reside beneath the surface areas of contact 104. In contrast, a tibial prosthesis with rails that reside directly beneath the surface area of load contact 104 would pose the disadvantage that the thickness of the tibial insert at that location would need to be increased to compensate for the recesses in which the rails would be received.

The tibial insert 20 is preferably thicker at its interior portion 21 as indicated in the drawings. In addition to the advantages produced by positioning the rails 46 and 48 between the surface areas of load contact 104, it is also advantageous to position the rail portion 46a, and correspondingly the recess portion 56a, as far as possible in the anterior direction, in part to take advantage of the benefits of the thicker anterior portion of the tibial insert 20. More particularly, this enables additional material force for transmitting forces to the rail portion 46a and maintaining strength in the tibial insert 20. It is further advantageous to have a sufficient space 108 between the recess 56 and the recess 58, for adequate material strength in transmitting the anterior-directed loading against the rail portion 46b.

It is to be understood that the concept of the rails 46 and 48 residing "between" the contact areas 104 shall refer broadly to the positioning of the rails 46 and 48 such that they do not reside beneath the contact areas 104 and such that they reside between imaginary vertical projections of the contact areas 104.

It will also be understood that the rails 46 and 48 reside at interior locations on the tibial plate 16. The rail 46 forms a T-shape, which may also be described as the portion 46b bisecting an imaginary line defined by the portion 46a at a bisect point that resides at an anterior location of the tibial plate. In the preferred embodiment shown, the bisect point would be item 43.

Figure 8:
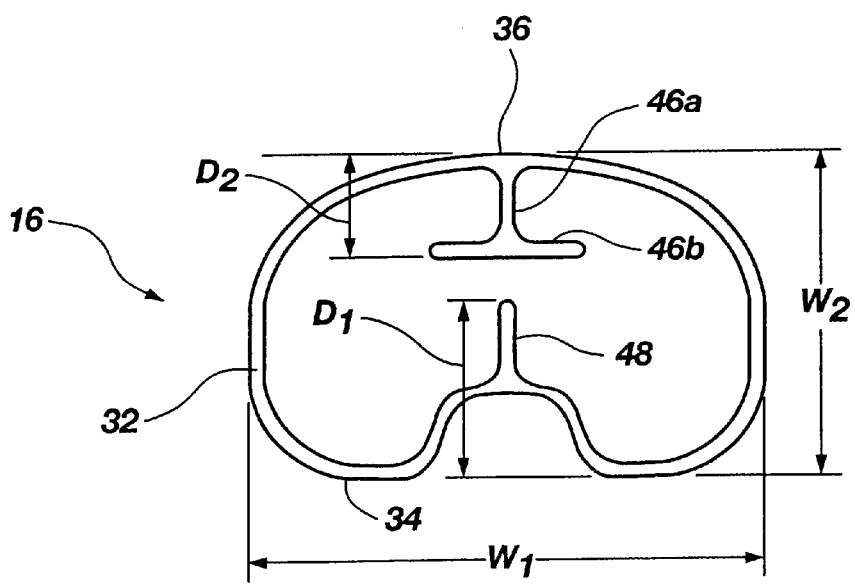
FIG. 8 is a plan view of the tibial plate of FIG. 3.

Referring now to FIG. 8, the length of the projection portion 46b is preferably a function of the medial-lateral width $W_1$ of the tibial plate 16, most preferably being in a range of twenty-five percent to thirty-one percent of said medial-lateral width $W_1$. The position of the poster-most portion of the projection portion 46b is preferably a function of the anterior-posterior width $W_2$, most preferably being positioned a distance $D_2$ from the anterior-most portion of sidewall 36 in a range of twenty-six percent to thirty-six percent of the anterior-posterior width $W_2$, in the posterior direction. The position of the anterior-most end of the projection 48 is preferably a function of the anterior-posterior width $W_2$, most preferably terminating at a position defining a distance $D_1$ from the posterior-most portion of sidewall 34 in a range of forty-five to sixty-five percent of said anterior-posterior width $W_2$, in the anterior direction. Most preferably, the distance $D_1$ is approximately forty-seven to forty-eight percent of the anterior-posterior width $W_2$.

In accordance with the features and combinations described above, a preferred method of repairing a knee joint includes the steps of:

(a) selecting a tibial plate having a proximal side, a distal side, and a keel extending outwardly from said distal side, and a first male projection formed on the proximal side of the tibial plate and a second male projection also formed on the proximal side of the tibial plate;

(b) inserting the keel into a proximal portion of a tibia;

(c) selecting an articular surface component having a proximal side and a first bearing surface and a second bearing surface formed on said proximal side;

(d) attaching the articular surface component to the proximal side of the tibial plate; and (e) placing first and second distal portions of a femur into slidable frictional contact with a first contact area of the first bearing surface and a second contact area of the second bearing surface, respectively, in an arrangement and position such that the first and second male projections reside between said first and second contact areas.

Another preferred method of repairing a knee joint includes the steps of:

(a) implanting a tibial plate into a proximal portion of a tibia, said tibial plate including at least one anterior locking flange;

(b) moving a tibial insert downwardly into an intermediate position upon the tibial plate, such that an anterior portion of said tibial insert resides above the anterior locking flange of the tibial plate, said tibial insert having at least one resilient anterior locking member also residing above the anterior locking flange of the tibial plate when said tibial insert reside in said intermediate position;

(c) inserting a first insert portion of a grasping device into a recess formed in an anterior side of the tibial insert, and inserting a second insert portion of the grasping device into a recess formed in an anterior side of the tibial plate; and (d) operating the grasping device to thereby squeeze the anterior sides of the tibial insert and tibial plate together, respectively, thereby causing the resilient anterior locking member of the tibial insert to engage into position beneath the anterior locking flange of the tibial plate.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A tibial prosthesis for implanting into a proximal portion of a tibia, said prosthesis comprising:

a tibial plate having a proximal side, a distal side, and a keel extending outwardly from said distal side for insertion into the proximal portion of the tibia;

a first, elongate male projection formed on the proximal side of the tibial plate and extending in a first direction;

a second, elongate male projection formed on the proximal side of the tibial plate and extending in a second, transverse direction relative to the first direction; and an articular surface component that is removably attachable to the proximal side of the tibial plate, said articular surface component having a distal side and a proximal side and a first elongate recess formed in the distal side and a second elongate recess also formed in said distal side, said first and second recesses being configured, dimensioned and positioned for simultaneously receiving the first and second elongate male projections therein, respectively, such that said male projections are thereby positioned to engage against sidewalls defining said recesses to thereby resist movement of the articular surface component in at least an anterior-posterior direction, a medial-lateral direction, and a rotational direction, and wherein the proximal side of the articular surface component further comprises a bearing surface for engaging in slidable frictional contact with a distal portion of a femur.

2. The prosthesis of claim 1, wherein the second elongate male projection bisects an imaginary line defined by the first elongate male projection at a bisect point that resides in an interior location of the tibial plate.

3. The prosthesis of claim 1, wherein the first elongate male projection resides in a substantially orthogonal orientation relative to the second elongate male projection.

4. The prosthesis of claim 1, wherein the first and second elongate male projections are joined together and collectively define a "T" shape.

5. The prosthesis of claim 1, further comprising a third, elongate male projection formed on the proximal side of the tibial plate.

6. The prosthesis of claim 5, wherein the second elongate male projection resides in a transverse direction relative to the first and third elongate male projections.

7. The prosthesis of claim 6, wherein the first and third elongate male projections reside in a substantially collinear orientation with each other.

8. The prosthesis of claim 5, wherein the first and second elongate male projections are positioned in a central, anterior section of the tibial plate, and wherein the third elongate projection is positioned in a central, posterior section of the tibial plate.

9. A tibial prosthesis for implanting into a proximal portion of a tibia, said prosthesis comprising:

a tibial plate having a proximal side, a distal side, and a keel extending outwardly from said distal side for insertion into the proximal portion of the tibia;

a medial sidewall extending upwardly from the proximal side of the tibial plate along a medial end of said proximal side, and a lateral sidewall extending upwardly from the proximal side of the tibial plate along a lateral end of said proximal side;

an articular surface component having a medial side edge and a lateral side edge and a distal side and a proximal side, said distal side being configured and dimensioned to reside between the medial and lateral sidewalls on the proximal side of the tibial plate in an operating position with the medial and lateral side edges of the articular surface component facing the medial and lateral sidewalls of the tibial plate, respectively;

locking means for locking the articular surface component into engagement with the proximal side of the tibial plate when said articular surface component resides in the operating position;

wherein the articular surface component and the sidewalls are positioned and arranged such that, when said articular surface component is locked into engagement in the operating position, a space resides between the medial sidewall on the tibial plate and the medial side edge of the articular surface component, and between the lateral sidewall on the tibial plate and lateral side edge of the articular surface component, respectively.

10. The prosthesis of claim 9, wherein no portion of the articular surface component resides in contact with the medial and lateral sidewalls on the tibial plate, when said articular surface component is locked into engagement with the proximal side of the tibial plate in the operating position.

11. A tibial prosthesis for implanting into a proximal portion of a tibia to facilitate contacting engagement of said prosthesis with first and second distal portions of a femur, said prosthesis comprising:

a tibial plate having a proximal side, a distal side, and a keel extending outwardly from said distal side for insertion into the proximal portion of the tibia;

a first male projection formed on the proximal side of the tibial plate;

an articular surface component that is attachable to the proximal side of the tibial plate in an operating position, said articular surface component having a proximal side and a first bearing surface and a second bearing surface formed on said proximal side for engaging in slidable frictional contact with the first and second distal portions of the femur at a first contact area and a second contact area, respectively, and wherein the first male projection is positioned and arranged to reside between said first and second contact areas when the articular surface component is disposed in the operating position, such that said first male projection is not in vertical alignment with said first and second contact areas.

12. The prosthesis of claim 11, further comprising a second, elongate male projection residing in a transverse orientation relative to the first male projection, said second male projection also being positioned and arranged to reside between said first and second contact areas when the articular surface component is disposed in the operating position, such that said second male projection is not in vertical alignment with said first and second contact areas.

13. The prosthesis of claim 12, further comprising a third, elongate male projection, said third male projection also being positioned and arranged to reside between said first and second contact areas when the articular surface component is disposed in the operating position, such that said third male projection is not in vertical alignment with said first and second contact areas.

14. The prosthesis of claim 13, wherein the articular surface component includes a distal side with recesses formed in said distal side for receiving the first, second and third male projections therein, respectively, such that said male projections are thereby positioned to engage against sidewalls defining said recesses to thereby resist movement of the articular surface component in at least an anterior-posterior direction, a medial-lateral direction, and a rotational direction.

15. The prosthesis of claim 12, wherein the second male projection comprises an elongate member and extends principally in a medial-lateral direction on the tibial plate.

16. The prosthesis of claim 11, said prosthesis being characterized by an absence of male projections residing in vertical alignment with the first contact area or the second contact area when the articular surface component resides in the operating position.

17. The prosthesis of claim 11, wherein the articular surface component is constructed from a polymeric material and is at least 6 mm thick at the first and second contact areas.

18. A tibial prosthesis for implanting into a proximal portion of a tibia, said prosthesis comprising:
a tibial plate having a proximal side, a distal side, and a keel extending outwardly from said distal side for insertion into the proximal portion of the tibia;
a first male projection formed on the proximal side of the tibial plate and in an anterior area of said proximal side, said first male projection having a portion extending in a medial-to-lateral direction; and
an articular surface component that is attachable to the proximal side of the tibial plate in an operating position, said articular surface component having a distal side and a proximal side and a first recess formed in the distal side, said first recess being configured, dimensioned and positioned for simultaneously receiving the first male projection thereinto, when the articular surface component resides in the operating position;
wherein a posterior-most portion of the medial-to-lateral portion of the male projection resides a distance from an anterior-most portion of the tibial plate that is within a range of twenty-six to thirty-six percent of an anterior-to-posterior width of said tibial plate.

19. The prosthesis of claim 18, further comprising a second male projection formed on the proximal side of the tibial plate, said second male projection having an anterior-most portion that resides a distance from a posterior-most portion of the tibial plate that is within a range of forty-five to sixty five percent of an anterior-to-posterior width of said tibial plate.

20. The prosthesis of claim 19, wherein the anterior-most portion of the second male projection resides a distance from a posterior-most portion of the tibial plate that is within a range of forty-seven to forty-eight percent of an anterior-to-posterior width of said tibial plate.

21. The prosthesis of claim 18, wherein the portion of the first male projection extending in a medial-to-lateral direction has a length that is within a range of twenty-five to thirty-one percent of a medial-to-lateral width of the tibial plate.

22. The prosthesis of claim 18, wherein the first male projection further comprises a first portion and a second portion, said first and second portions collectively comprising a "T" shape.

23. The prosthesis of claim 22, further comprising a second male projection, wherein the first portion of the first male projection and the second male projection reside in a substantial collinear orientation with each other and in the anterior-posterior direction.

24. A tibial prosthesis for implanting into a proximal portion of a tibia, said prosthesis comprising:
a tibial plate having a proximal side, a distal side, and a keel extending outwardly from said distal side for insertion into the proximal portion of the tibia;
a male projection formed on the proximal side of the tibial plate and in a posterior area of said proximal side; and
an articular surface component that is attachable to the proximal side of the tibial plate in an operating position, said articular surface component having a distal side and a proximal side and a recess formed in the distal side, said recess being configured, dimensioned and positioned for simultaneously receiving the male projection thereinto, when the articular surface component resides in the operating position;
wherein said male projection has an anterior-most portion that resides a distance from a posterior-most portion of the tibial plate that is within a range of forty-five to sixty-five percent of an anterior-to-posterior width of said tibial plate.

25. The prosthesis of claim 24, further comprising a second male projection formed on the proximal side of the tibial plate, said second male projection have an anterior-most portion that resides a distance from a posterior-most portion of the tibial plate that is within a range of forty-five to sixty five percent of an anterior-to-posterior width of said tibial plate.

26. A tibial prosthesis for implanting into a proximal portion of a tibia, said prosthesis comprising:
a tibial plate having a proximal surface, a distal surface, and a keel extending outwardly from said distal side for insertion into the proximal portion of the tibia;
an articular surface component that is attachable to the proximal side of the tibial plate in an operating position in contact upon said proximal side of said tibial plate, said articular surface component having a distal surface and a proximal surface, and wherein the proximal surface of the articular surface component further comprises a bearing surface for engaging in slidable frictional contact with a distal portion of a femur;
locking means for locking the articular surface component into engagement with the tibial plate by operation of downward vertical movement of said articular surface component into contact with said tibial plate; and
a posterior sidewall extending upwardly from the tibial plate and an anterior sidewall extending upwardly from said tibial plate, wherein the locking means further comprises a posterior holding flange extending outwardly from the posterior sidewall, and a depressable flange extending outwardly from a posterior edge of the articular surface component.

27. The prosthesis of claim 26, wherein the depressable flange resides beneath and in contact with the posterior holding flange when the articular surface component resides in the operating position.

28. The prosthesis of claim 27, wherein the depressable flange has a proximal surface residing a distance $d_1$ from the distal surface of the articular surface component when said depressable flange is in a natural, unbiased position, and wherein the posterior holding flange has a distal surface residing a distance $d_2$ from the proximal surface of the tibial plate, and wherein the distance $d_1$ is greater than the distance $d_2$ to thereby cause the posterior holding flange to press downwardly upon the depressable flange and hold said depressable flange in a depressed position to produce a compressive interference fit between said depressable flange and posterior holding flange when the depressable flange resides beneath and in contact with the posterior holding flange.

29. The prosthesis of claim 26, wherein the locking means further comprises a resilient locking member extending in a downward direction from an anterior edge of the articular surface component, and an anterior holding flange extending outwardly from the anterior sidewall.

30. The prosthesis of claim 29, wherein the resilient locking member further comprises a distal locking flange and wherein the tibial plate and sidewalls and the articular surface component are all configured and dimensioned such that the distal locking flange resides beneath and in contact with the anterior holding flange when the articular surface component resides in the operating position.

31. The prosthesis of claim 30, wherein the resilient locking member is depressable in an anterior-posterior direction and wherein a distal-anterior side of the distal locking flange comprises a beveled edge, and wherein the articular surface component is configured and dimensioned such that insertion of the depressable flange beneath the posterior holding flange followed by downward vertical movement of the locking piece into the operating position causes sliding frictional engagement of said beveled edge against the anterior holding flange and consequent depression of the resilient locking member in a posterior direction followed by a snap-lock movement of the distal locking flange in an anterior direction into place beneath the anterior holding flange.

32. A tibial prosthesis system comprising:
a tibial plate having a proximal surface, a distal surface, and a keel extending outwardly from said distal side for insertion into the proximal portion of the tibia;
an articular surface component that is attachable to the proximal side of the tibial plate in an operating position in contact upon said proximal side of said tibial plate, said articular surface component having a distal surface and a proximal surface, and wherein the proximal surface of the articular surface component further comprises a bearing surface for engaging in slidable frictional contact with a distal portion of a femur;
locking means for locking the articular surface component into engagement with the tibial plate by operation of downward vertical movement of said articular surface component into contact with said tibial plate; and
a grasping device for squeezing together the tibial plate and the articular surface component during attaching of said articular surface component to said tibial plate.

33. A tibial prosthesis for implanting into a proximal portion of a tibia, said prosthesis comprising:
a tibial plate having a proximal side, a distal side, and a keel extending outwardly from said distal side for insertion into the proximal portion of the tibia;
an articular surface component that is attachable upon the proximal side of the tibial plate in an operating position in contact upon said proximal side of said tibial plate, said articular surface component having a distal side and a proximal side, and wherein the proximal side of the articular surface component further comprises a bearing surface for engaging in slidable frictional contact with a distal portion of a femur; and
locking means for locking the articular surface component into engagement with the tibial plate by operation of a compressive interference fit between a portion of the articular surface component and a portion of the tibial plate.

34. The prosthesis of claim 33, further comprising a posterior sidewall extending upwardly from the tibial plate and an anterior sidewall extending upwardly from said tibial plate, wherein the locking means further comprises a posterior holding flange extending outwardly from the posterior sidewall, and a depressable flange extending outwardly from a posterior edge of the articular surface component.

35. The prosthesis of claim 34, wherein the depressable flange resides beneath and in contact with the posterior holding flange when the articular surface component resides in the operating position.

36. The prosthesis of claim 35, wherein the depressable flange has a proximal surface residing a distance $d_1$ from the distal surface of the articular surface component when said depressable flange is in a natural, unbiased position, and wherein the posterior holding flange has a distal surface residing a distance $d_2$ from the proximal surface of the tibial plate, and wherein the distance $d_1$ is greater than the distance $d_2$ to thereby cause the posterior holding flange to press downwardly upon the depressable flange and hold said depressable flange in a depressed position to produce a compressive interference fit between said depressable flange and posterior holding flange when the depressable flange resides beneath and in contact with the posterior holding flange.

37. The prosthesis of claim 34, wherein the locking means further comprises a resilient locking member extending in a downward direction from an anterior edge of the articular surface component, and an anterior holding flange extending outwardly from the anterior sidewall.

38. The prosthesis of claim 37, wherein the resilient locking member further comprises a distal locking flange and wherein the tibial plate and sidewalls and the articular surface component are all configured and dimensioned such that the distal locking flange resides beneath and in contact with the anterior holding flange when the articular surface component resides in the operating position.

39. The prosthesis of claim 38, wherein the resilient locking member is depressable in an anterior-posterior direction and wherein a distal-anterior side of the distal locking flange comprises a beveled edge, and wherein the articular surface component is configured and dimensioned such that insertion of the depressable flange beneath the posterior holding flange followed by downward vertical movement of the locking piece into the operating position causes sliding frictional engagement of said beveled edge against the anterior holding flange and consequent depression of the resilient locking member in a posterior direction followed by a snap-lock movement of the distal locking flange in an anterior direction into place beneath the anterior holding flange.

40. A tibial prosthesis for implanting into a proximal portion of a tibia, said prosthesis comprising:
a tibial plate having a proximal side, a distal side, and a keel extending outwardly from said distal side for insertion into the proximal portion of the tibia;
an articular surface component that is attachable upon the proximal side of the tibial plate in an operating position in contact upon said proximal side of said tibial plate, said articular surface component having a distal side and a proximal side, and wherein the proximal side of the articular surface component further comprises a bearing surface for engaging in slidable frictional contact with a distal portion of a femur; and
locking means for locking the articular surface component into engagement with the tibial plate by operation of a clamping fit between a portion of the articular surface component and a portion of the tibial plate.

41. The prosthesis of claim 40, further comprising:
a male projection formed on the proximal side of the tibial plate; and
a recess formed in the distal side of the articular surface component and being configured, dimensioned and positioned for receiving the male projection therein when the articular surface component resides in the operating position;
wherein the recess has a smaller width than a width of the male projection such that sidewalls defining said recess operate to clamp upon the male projection when said male projection is placed into said recess.

42. The prosthesis of claim 40, further comprising:
a T-shaped male projection formed on the proximal side of the tibial plate, and a straight-line male projection also formed on said proximal side of said tibial plate; and
a T-shaped recess and a straight-line recess formed in the distal side of the articular surface component, said recesses being configured, dimensioned and positioned for receiving the T-shaped male projection and the straight-line male projection therein, respectively, when the articular surface component resides in the operating position;
wherein the recesses have smaller widths than widths of the male projections received in said recesses, respectively, such that sidewalls defining said recesses operate to clamp upon the male projections when said male projections are placed into said recesses.

43. A tibial prosthesis for implanting into a proximal portion of a tibia, said prosthesis comprising:
a tibial plate having a proximal side, a distal side, and a keel extending outwardly from said distal side for insertion into the proximal portion of the tibia;
a first male projection formed on the proximal side of the tibial plate, said projection extending principally in a medial-lateral direction; and
an articular surface component that is attachable to the proximal side of the tibial plate, said articular surface component having a distal side and a proximal side and a first recess formed in the distal side, said first recess being configured, dimensioned and positioned for receiving the first male projection therein such that sidewalls defining the first recess are engageable with a posterior-facing surface of the first male projection to thereby cause said first male projection to block movement of the articular surface component in the anterior-posterior direction.

44. The prosthesis of claim 43, wherein the posterior-facing surface of the first male projection has a length that is with a range of twenty-five to thirty-one percent of a medial-to-lateral width of the tibial plate.

45. A tibial prosthesis for implanting into a proximal portion of a tibia, said prosthesis comprising:
a tibial plate having a proximal side, a distal side, and a keel extending outwardly from said distal side for insertion into the proximal portion of the tibia;
a first, elongate male projection formed on the proximal side of the tibial plate and extending in a first direction;
a second, elongate male projection formed on the proximal side of the tibial plate and extending in a second, transverse direction relative to the first direction; and
an articular surface component that is removably attachable to the proximal side of the tibial plate in an operating position, said articular surface component having a distal side and a proximal side and a first elongate recess formed in the distal side and a second elongate recess also formed in said distal side, said first and second recesses being configured, dimensioned and positioned for simultaneously receiving the first and second elongate male projections therein, respectively, such that said male projections are thereby positioned to engage against sidewalls defining said recesses to thereby resist movement of the articular surface component in at least an anterior-posterior direction, a medial-lateral direction, and a rotational direction, and wherein the proximal side of the articular surface component further comprises a bearing surface for engaging in slidable frictional contact with a distal portion of a femur;
wherein the second elongate male projection bisects an imaginary line defined by the first elongate male projection at a bisect point that resides in an interior location of the tibial plate;
wherein the first elongate male projection resides in a substantially orthogonal orientation relative to the second elongate male projection;
wherein the first and second elongate male projections are joined together and collectively define a "T" shape;
further comprising a third, elongate male projection formed on the proximal side of the tibial plate;
wherein the second elongate male projection resides in a transverse direction relative to the first and third elongate male projections;
wherein the first and third elongate male projections reside in a substantially collinear orientation with each other;
wherein the first and second elongate male projections are positioned in a central, anterior section of the tibial plate, and wherein the third elongate projection is positioned in a central, posterior section of the tibial plate;
wherein the articular surface component has a proximal side and a first bearing surface and a second bearing surface formed on said proximal side for engaging in slidable frictional contact with first and second distal portions of a femur at a first contact area and a second contact area, respectively, and wherein the first male projection is positioned and arranged to reside between said first and second contact areas when the articular surface component is disposed in the operating position, such that said first male projection is not in vertical alignment with said first and second contact areas;

wherein the articular surface component is constructed from a polymeric material and is at least 6 mm thick at the first and second contact areas;

wherein a posterior-most portion of the second, elongate male projection resides a distance from an anterior-most portion of the tibial plate that is within a range of twenty-six to thirty-six percent of an anterior-to-posterior width of said tibial plate;

wherein the third, elongate male projection includes an anterior-most portion that resides a distance from a posterior-most portion of the tibial plate that is within a range of forty-five to sixty five percent of an anterior-to-posterior width of said tibial plate;

wherein the second, elongate male projection has a length that is within a range of twenty-five to thirty-one percent of a medial-to-lateral width of the tibial plate;

locking means for locking the articular surface component into engagement with the tibial plate by operation of a compressive interference fit between a portion of the articular surface component and a portion of the tibial plate;

a posterior sidewall extending upwardly from the tibial plate and an anterior sidewall extending upwardly from said tibial plate, wherein the locking means further comprises a posterior holding flange extending outwardly from the posterior sidewall, and a depressable flange extending outwardly from a posterior edge of the articular surface component;

wherein the depressable flange resides beneath and in contact with the posterior holding flange when the articular surface component resides in the operating position;

wherein the depressable flange has a proximal surface residing a distance $d_1$ from the distal surface of the articular surface component when said depressable flange is in a natural, unbiased position, and wherein the posterior holding flange has a distal surface residing a distance $d_2$ from the proximal surface of the tibial plate, and wherein the distance $d_1$ is greater than the distance $d_2$ to thereby cause the posterior holding flange to press downwardly upon the depressable flange and hold said depressable flange in a depressed position to produce a compressive interference fit between said depressable flange and posterior holding flange when the depressable flange resides beneath and in contact with the posterior holding flange;

wherein the locking means further comprises a resilient locking member extending in a downward direction from an anterior edge of the articular surface component, and an anterior holding flange extending outwardly from the anterior sidewall;

wherein the resilient locking member further comprises a distal locking flange and wherein the tibial plate and sidewalls and the articular surface component are all configured and dimensioned such that the distal locking flange resides beneath and in contact with the anterior holding flange when the articular surface component resides in the operating position;

wherein the resilient locking member is depressable in an anterior-posterior direction and wherein a distal-anterior side of the distal locking flange comprises a beveled edge, and wherein the articular surface component is configured and dimensioned such that insertion of the depressable flange beneath the posterior holding flange followed by downward vertical movement of the locking piece into the operating position causes sliding frictional engagement of said beveled edge against the anterior holding flange and consequent depression of the resilient locking member in a posterior direction followed by a snap-lock movement of the distal locking flange in an anterior direction into place beneath the anterior holding flange;

clamp-locking means for locking the articular surface component into engagement with the tibial plate by operation of a clamping fit between a portion of the articular surface component and a portion of the tibial plate;

wherein the first and second recesses have a smaller width than a width of the first and second male projections such that sidewalls defining said first and second recesses operate to clamp upon the first and second male projections, respectively, when said male projections are placed into said recesses.

46. A tibial prosthesis system comprising: the prosthesis of claim 45, said tibial prosthesis system further comprising a grasping device for squeezing together the tibial plate and the articular surface component during attaching of said articular surface component to said tibial plate.

47. A method of repairing a knee joint, said method comprising the steps of:

(a) selecting a tibial plate having a proximal side, a distal side, and a keel extending outwardly from said distal side, and a first male projection formed on the proximal side of the tibial plate and a second male projection also formed on the proximal side of the tibial plate;

(b) inserting the keel into a proximal portion of a tibia;

(c) selecting an articular surface component having a proximal side and a first bearing surface and a second bearing surface formed on said proximal side;

(d) attaching the articular surface component to the proximal side of the tibial plate; and (e) placing first and second distal portions of a femur into slidable frictional contact with a first contact area of the first bearing surface and a second contact area of the second bearing surface, respectively, in an arrangement and position such that the first and second male projections reside between said first and second contact areas.

48. A method of repairing a knee joint, said method comprising the steps of:

(a) implanting a tibial plate into a proximal portion of a tibia, said tibial plate including at least one anterior locking flange;

(b) moving a tibial insert downwardly into an intermediate position upon the tibial plate, such that an anterior portion of said tibial insert resides above the anterior locking flange of the tibial plate, said tibial insert having at least one resilient anterior locking member also residing above the anterior locking flange of the tibial plate when said tibial insert reside in said intermediate position;

(c) inserting a first insert portion of a grasping device into a recess formed in an anterior side of the tibial insert, and inserting a second insert portion of the grasping device into a recess formed in an anterior side of the tibial plate; and (d) operating the grasping device to thereby squeeze the anterior sides of the tibial insert and tibial plate together, respectively, thereby causing the resilient anterior locking member of the tibial insert to engage into position beneath the anterior locking flange of the tibial plate.

49. The method of claim 48, wherein step (d) further comprises forcing male projections formed on the tibial plate into recesses formed in a distal surface of the tibial insert.

50. The method of claim 48, wherein step (b) further comprises inserting a posterior flange of the tibial insert into a space beneath a posterior holding flange of the tibial plate to place the tibial insert into the intermediate position.

* * * * *